United States Patent [19]

Tokoyama

[11] Patent Number: 5,261,285
[45] Date of Patent: Nov. 16, 1993

[54] POWDER GRANULE SAMPLE INSPECTION APPARATUS

[75] Inventor: Katsumi Tokoyama, Osaka, Japan

[73] Assignee: Hajime Industries Ltd., Tokyo, Japan

[21] Appl. No.: 854,741

[22] Filed: Mar. 18, 1992

Related U.S. Application Data

[63] Continuation of Ser. No. 742,087, Aug. 2, 1991, abandoned, which is a continuation of Ser. No. 561,896, Aug. 2, 1990, abandoned.

[51] Int. Cl.$^5$ ............................................. G01M 19/00
[52] U.S. Cl. ................................................. 73/865.8
[58] Field of Search ............... 73/864.81, 865.5, 865.8; 209/580–582; 198/339.1, 340, 341, 803.16; 358/106, 107; 241/68, 117, 118, 101.3

[56] References Cited

U.S. PATENT DOCUMENTS

| | | | |
|---|---|---|---|
| 1,862,436 | 6/1932 | Schmiedeknecht | 241/118 |
| 3,770,111 | 11/1973 | Greenwood et al. | 209/580 |
| 4,602,745 | 7/1986 | Maliszewski et al. | 241/117 |
| 4,643,366 | 2/1987 | Soma et al. | 241/117 |
| 4,726,898 | 2/1988 | Mills et al. | 209/581 |
| 4,776,466 | 10/1980 | Yoshida | 358/106 |
| 4,884,463 | 12/1989 | Kay | 73/865.8 |
| 4,946,046 | 8/1990 | Affleck et al. | 209/580 |
| 5,050,808 | 9/1991 | Satake et al. | 242/101.3 |

FOREIGN PATENT DOCUMENTS 0021046 1/1987 Japan ..................... 358/106

*Primary Examiner*—Robert Raevis
*Attorney, Agent, or Firm*—Bauer & Schaffer

[57] ABSTRACT

Powder granule samples are continuously and automatically inspected on a rotary table which conveys the granule specimens on its suface. The rotary table has a circular 5 groove formed on its surface in which the sample granules will fit.

5 Claims, 8 Drawing Sheets

POWDER GRANULE SAMPLE INSPECTION APPARATUS

This is a continuation of Ser. No. 742,087, filed: Aug. 2, 1991, now abandoned, which is a continuation of Ser. No. 561,896 filed Aug. 2. 1990, now abandoned.

BACKGROUND OF THE INVENTION

1. Field of the Invention

The present invention relates generally to powder granule inspection apparatuses that automatically inspect more than one category of such powder granule samples as pharmaceutical material, plastic materials or the like.

2. Description of the Prior Art

The inspection of the powder granule samples such as pharmaceutical materials, plastic materials or the like, for such items as existence or not of metallic foreign particles, mixture of coloured foreign particles with number and size thereof, moisture content, etc. were conventionally respectively done as separate manual operations. For this reason, in order to conduct a plural item inspection on the powder granule samples, man power and time were consumed so that the sample characteristics could change during the inspection to an extent that the obtained inspection data would reflect an inferior precision.

Therefore, the applicant for the present application has developed a powder granule sample inspection apparatus that can continuously and automatically conduct such plural items of inspection as above mentioned on powder granule sample as Japanese Utility Model application No. 63-15481.

As shown on FIG. 1, such powder granule sample inspection apparatus starts by dropping the powder granule sample inside a connection tube 60 during which the existence or not of metallic foreign particles were inspected by metal detector 61. Then the dropped sample was loaded onto a conveying means which in this case was the surface of a belt conveyer 62 to be transferred by a certain distance during which time inspection was conducted by inspection equipment that is placed above belt conveyer 62, such as a moisture gauge 63 and television camera 64 equipped with strobo for inspections of the moisture content and number and size of coloured foreign particles. Further, the applicant of the present application has developed a powder granule sample inspection apparatus that uses a hard and flat surfaced rotary table in lieu of the belt conveyer 62 shown in FIG. 1 with a purpose to prevent the mixture of the sample after inspection with the sample before inspection in order to secure the obtainment of inspection data with high reliability, and to enable a virtually complete removal of the sample that was inspected from the surface of the conveying means. Further purposes to prevent the erroneous detection of the sample shades when inspecting the sample on the surface of the rotary table for coloured foreign particles by the strobo irradiation from the above so that the shade is thrown on the surface of the rotary table, a semi transparent rotary table that passes light is adopted with the strobo irradiation from the front and back surfaces of the rotary table.

However, since such above mentioned rotary table of powder granule sample inspection apparatus has a hard and flat surface, when vibration is applied to the rotary table, the sample granules on the surface will tumble or move so that there is the fear of falling off from the rotary table surface before the inspection and will not pass under the inspection equipment to an extent that the entire volume of the sample that was supplied on the rotary table surface would not be inspected and there was the problem that such obtained inspection data lacked the reliability.

OBJECTS AND SUMMARY OF THE PRESENT INVENTION

Therefore, it is an object of the present invention to propose a powder granule inspection apparatus that solves such above mentioned problems which enables the obtainment of inspection data with high reliability.

According to the first aspect of the present invention, there is a powder granule sample inspection apparatus that continuously and automatically conducts the inspection of powder granule sample inspection, comprising:

(a) a rotary table which conveys the powder granule sample on its surface for a certain distance; and
(b) an inspection system that inspects at least one of inspection items of the said sample during its conveyance; said rotary table having formed on its surface a circular-shaped groove to which the sample granule will fit.

The additional, and other objects, features and advantages of the present invention will become apparent from the following description taken in conjunction with the accompanying drawings.

DESCRIPTION OF THE PREFERRED EMBODIMENTS

Figure 2:
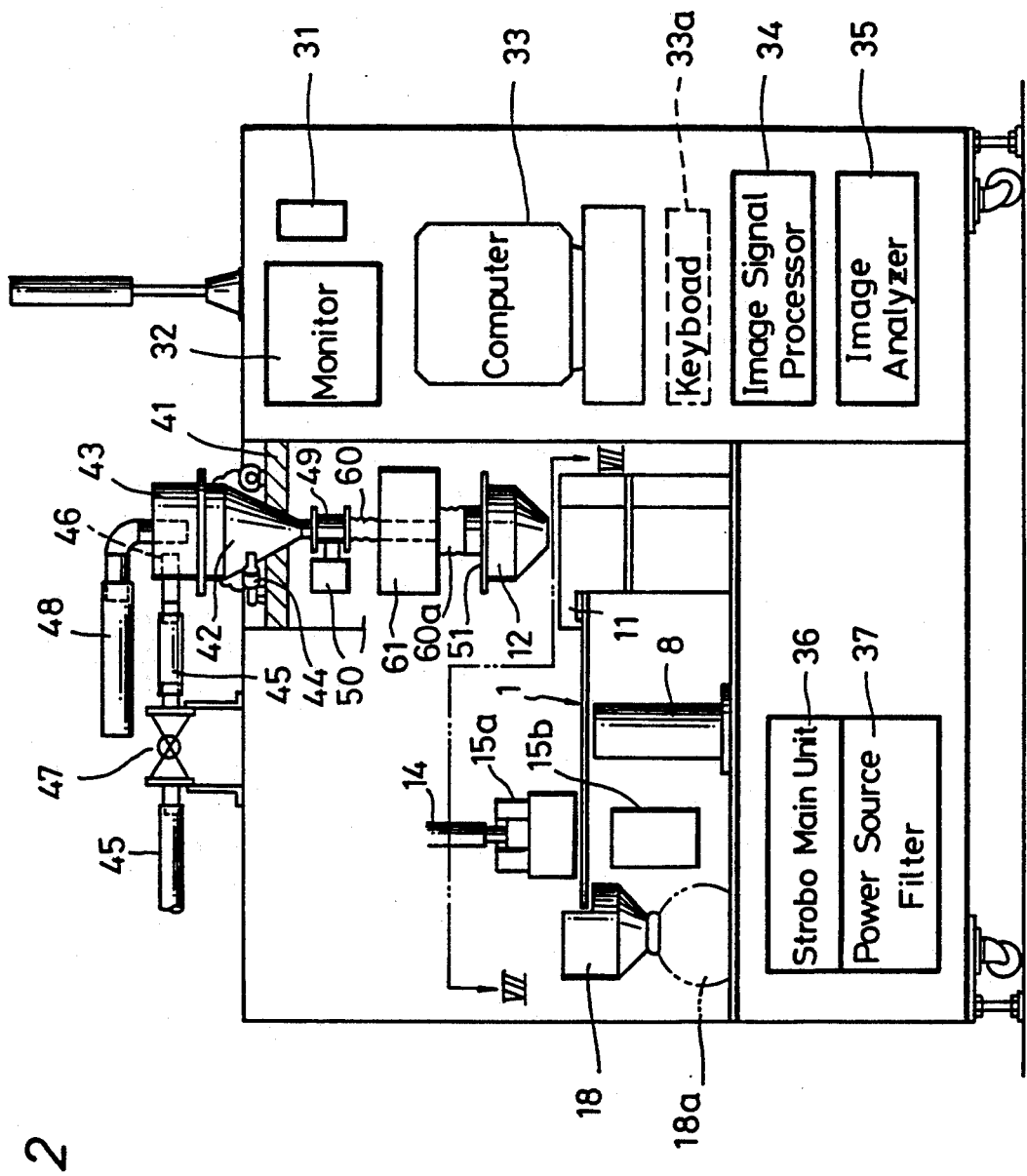
FIG. 2 is a partial cross sectional side view that shows an example of the powder granule sample inspection apparatus according to the present invention.
Figure 3:
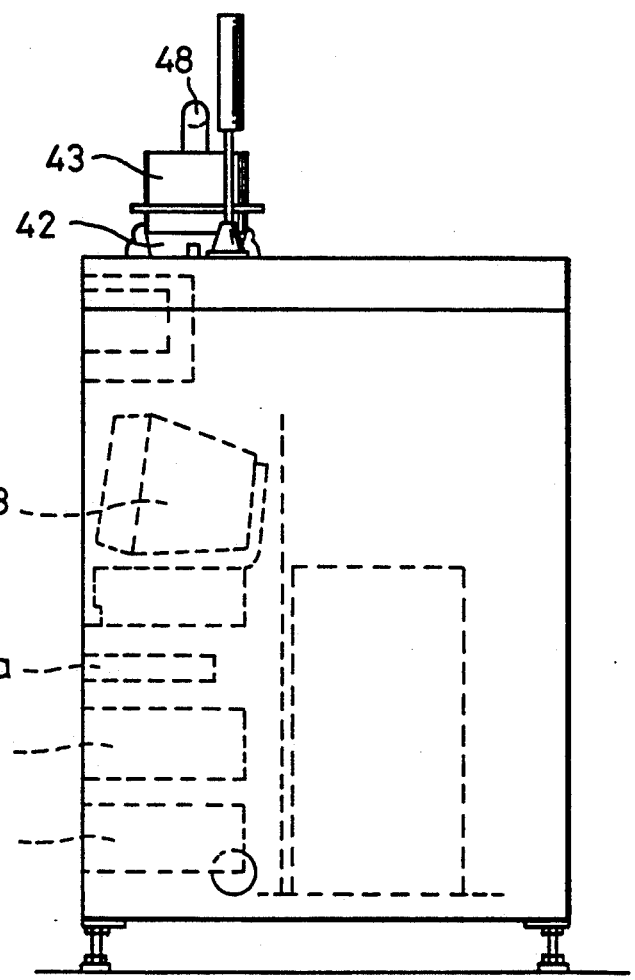
FIG. 3 is a front view thereof.
Figure 4:
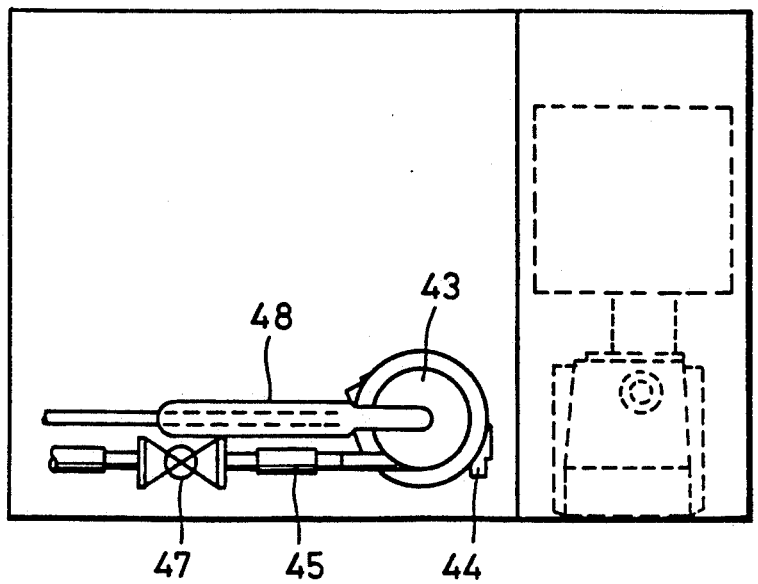
FIG. 4 is a top view thereof.
Figure 5:
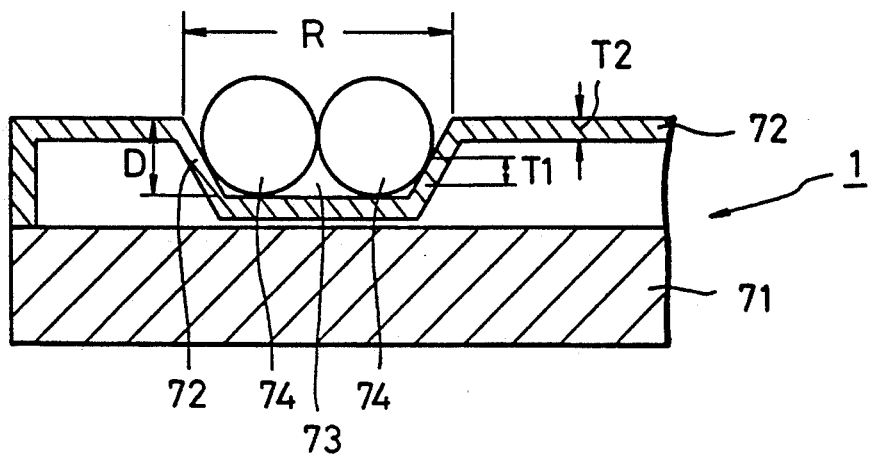
FIG. 5 shows a partial cross-sectional of a rotary table.

An example of the present invention will be explained hereunder. FIG. 2 is a partial cross-sectional side view showing an embodiment of the powder granule sample inspection apparatus according to the present invention, FIG. 3 is a front view of the same, FIG. 4 is a top plan view of the same. Further, FIG. 5 is a partial vertical cross-sectional diagram showing a rotary table 1 used in the example of the present invention, and FIG. 6 is a top plan view of the same.

Rotary table 1 is a disc type double layer structure whereon the surface of transparent glass plate 71 and an acrylic film 72 that can transmit light which is hard and is semi transparent milky white coloured are mounted so that the total structure is semi transparent.

Figure 6:
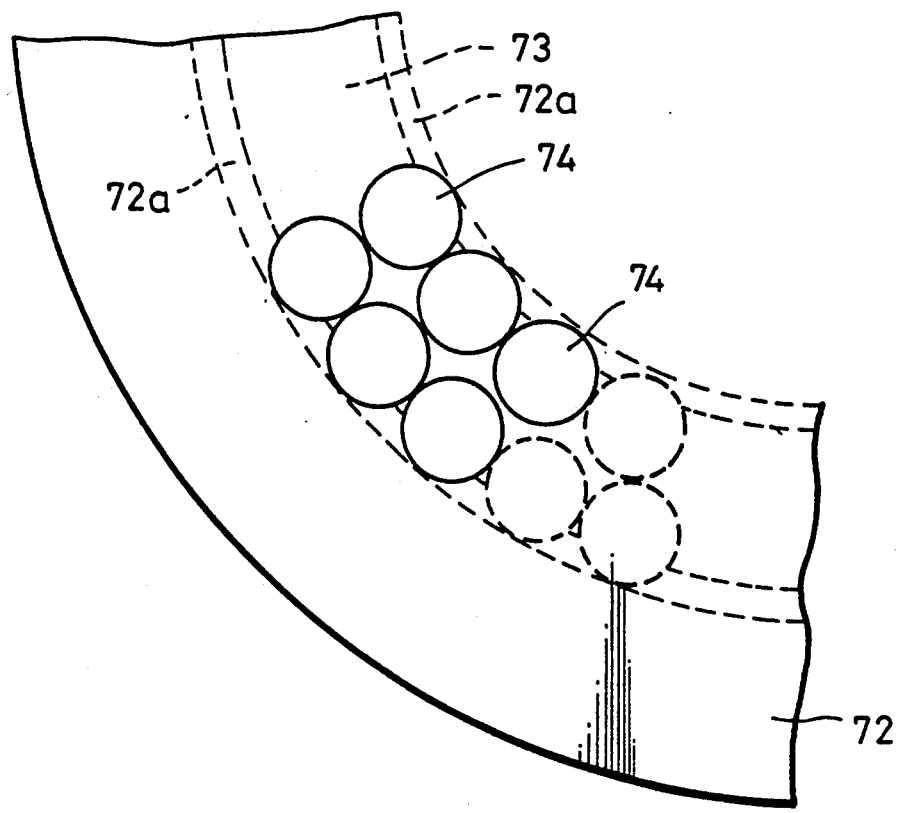
FIG. 6 is a top view thereof.
Figure 7:
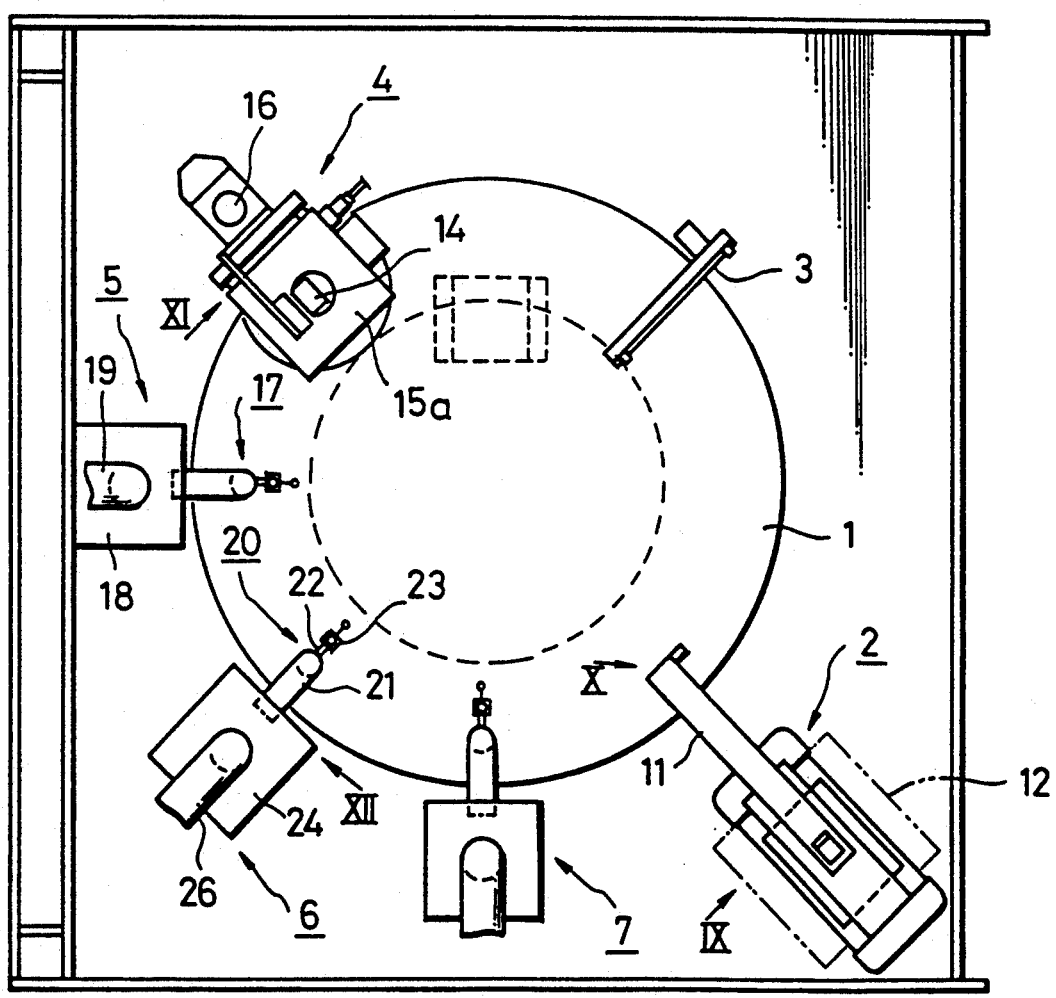
FIG. 7 is a view showing a portion of FIG. 2 indicated by an arrow line VII—VII.

Further, on the acrylic film 72 a reversed trapezoid cross sectioned groove 73 is formed in a circular shape by bending the acrylic film 72 as shown on FIG. 6. In this case, the groove 73 is formed with a depth D that is slightly smaller than the diameter of each sample granule 74 as well as a width R so that 2 pieces of the sample granule 74 will fit in the groove 73 as lined up side by side. Also, the surface of acrylic film 72 is flat excepting the groove 73. At the same time, the thickness of the tapered portion 72a of the acrylic film 72 that forms the groove 73 is selected to be such a thickness that will not generate any shadow on the surface of the acrylic film 72 even when a strobo irradiation on the groove 73 portion is made from the back side of the rotary table 1 (under the glass plate 71 in FIG. 5), which is to say that it is made with a thickness that no shadow of the taper portion 72a shall be detected when the groove 73 portion of the acrylic film 72 is photosensed by a television camera from above. To be practical, it is formed so that the thickness T1 of the taper shaped portion 72a in the vertical direction is selected to be about the same to the layer thickness T2 of the acrylic film 72 that does not form the groove 73. Further, FIG. 7 is a cross-sectional view showing a part of FIG. 2 indicated by an arrow line VII—VII. In FIG. 7, around the circumference of the rotary table 1, a feeder 2 which supplies the samples in a manner to fit into the groove 73 on the surface of rotary table 1, static electricity remover 3 that removes the static electricity of the sample in the groove 73, coloured foreign particle inspector 4 which detects the number and size of coloured foreign particles that are contained in the sample, coloured foreign particle remover 5 which absorbs and removes the coloured foreign particles contained in the sample, as well as sample removers 6, 7 which equally absorb and remove the sample from the surface of rotary table 1, are respectively installed.

Figure 8:
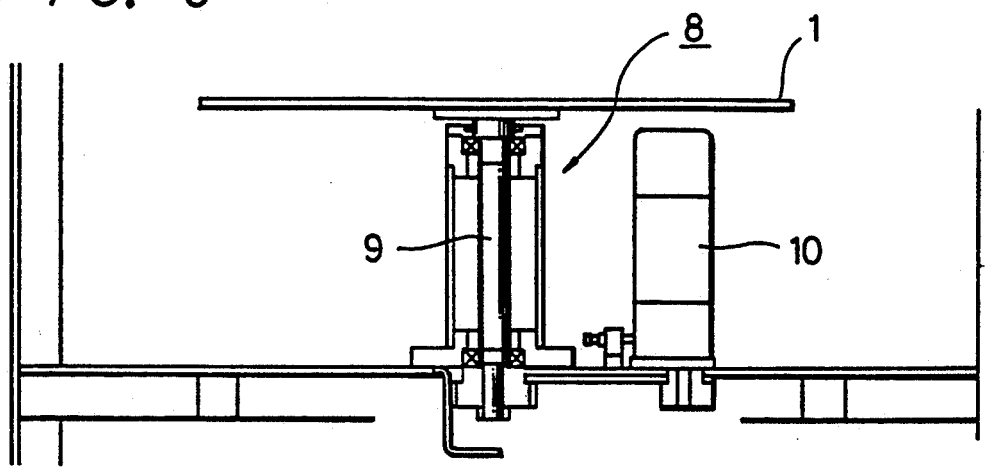
FIG. 8 is a vertical cross-sectional view showing a rotation drive mechanism.
Figure 9:
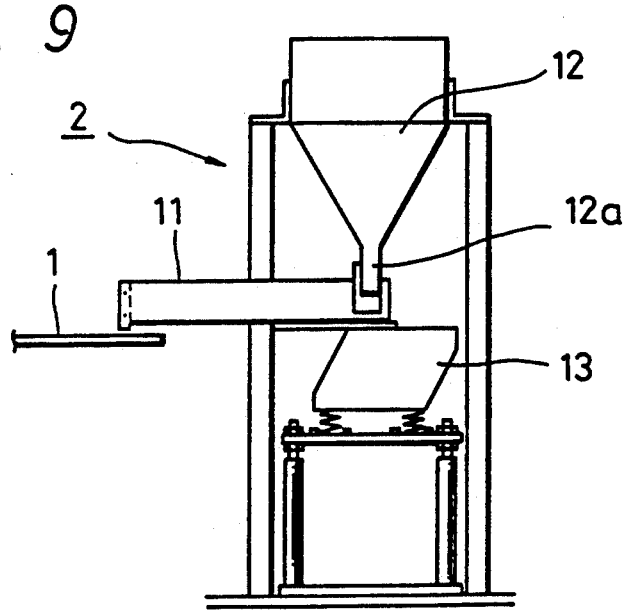
FIG. 9 is a view showing a portion of FIG. 7 indicated by an arrow IX.
Figure 10:
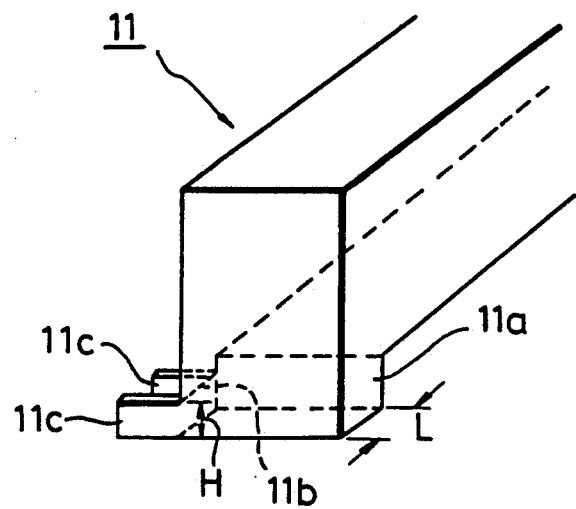
FIG. 10 is a view showing a portion of FIG. 7 indicated by an arrow X.

Under the rotary table 1, a rotation drive mechanism 8 as shown on FIG. 8 is installed. The rotation drive mechanism 8 is equipped with a rotation shaft 9 which is located in the perpendicular direction and connected to the center of rotary table 1 and a motor 10 which rotates the rotation shaft 9 at a predetermined speed. FIG. 9 is a diagram showing a portion of FIG. 7 indicated by an arrow IX and generally shows the feeder 2. In FIG. 9, 11 is a through which is a tube body with a square shaped cross section, whereat a hopper 12 above its upper end and a magnetic coil 13 which provides vibration to trough 11 at its lower part are installed. A bottom exhaust outlet 12a of hopper 12 is placed inside trough 11 by passing the opening formed through the top wall of trough 11. The other end of trough 11 is placed on the rotary table 1 as shown on FIG. 10 which shows the portion indicated by an arrow X in FIG. 7. In other words, the other end of the above mentioned trough 11 is closed in the lengthwise direction and a protruding tube part 11a at L dimension in the lengthwise direction is communicated with the other end portion of trough 11 at its lower surface. Also the protruding tube part 11a is open downwards where such down faced opening is placed to face the surface of rotary table 1 so that it covers groove 73 of film 72. The space between the down faced opening and the surface of the rotary table 1 is so selected that the perpendicular distance from the bottom of groove 73 up to the down faced opening is smaller than the sample granule diameter. Further, in the rotation direction of rotary table 1 at the under side of the protruding tube part 11a there is an opening 11b formed at a height of H size, whereas extensions 11c at both sides of the opening 11b are formed in the rotation direction. In this case, the distance L between the extensions 11c is slightly larger than the width R of groove 73, while the dimension H is so selected that the vertical distance from the bottom of groove 73 to the top side of opening 11b is slightly larger than the diameter of the sample granule.

Figure 11:
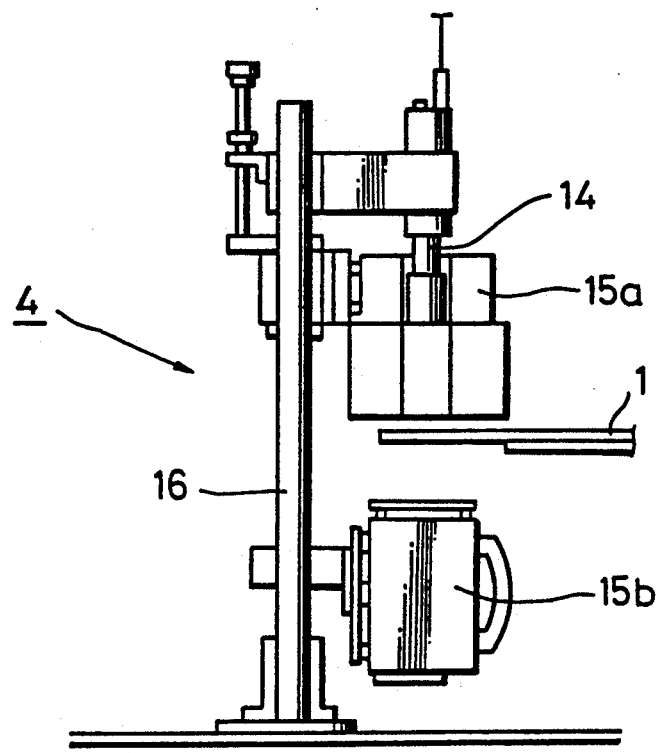
FIG. 11 is a view showing a portion of FIG. 7 indicated by an arrow XI.

FIG. 11 shows a part of FIG. 7 as indicated by an arrow XI, namely the coloured foreign particle inspection system 4. This coloured foreign particle inspection system 4 is equipped with a television camera 14 and a pair of strobos 15a, 15b. Strobo 15a is placed above rotary table 1 with the television camera 14 while strobo 15b is placed under the rotary table 1 in a manner that counter faces the strobo 15a. 16 is the stand that supports up and down elevation of television camera 14, strobos 15a and 15b.

Figure 1:
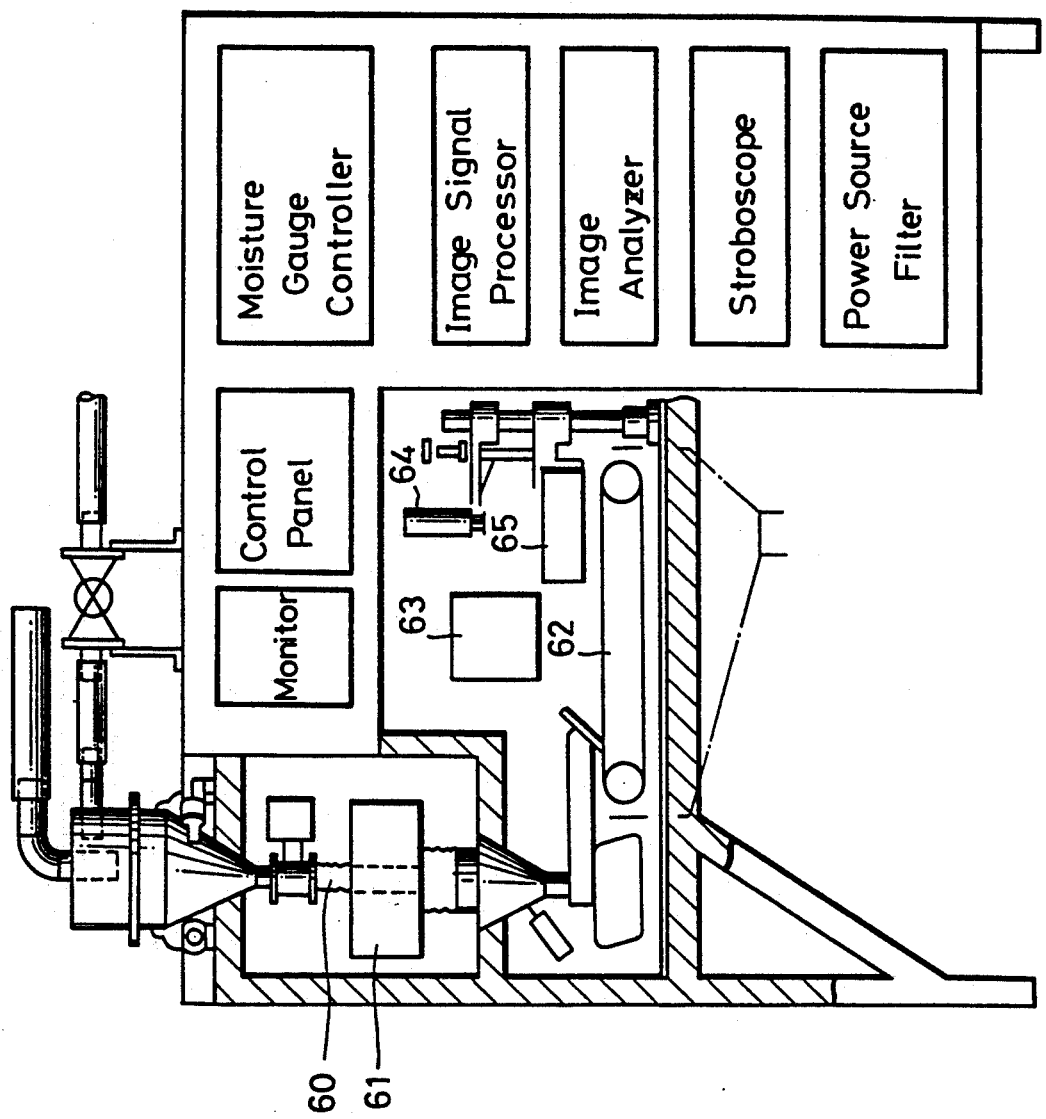
FIG. 1 is a partial cross-sectional view that shows an example of a powder granule sample inspection apparatus which was proposed by the applicant of the present application.
Figure 12:
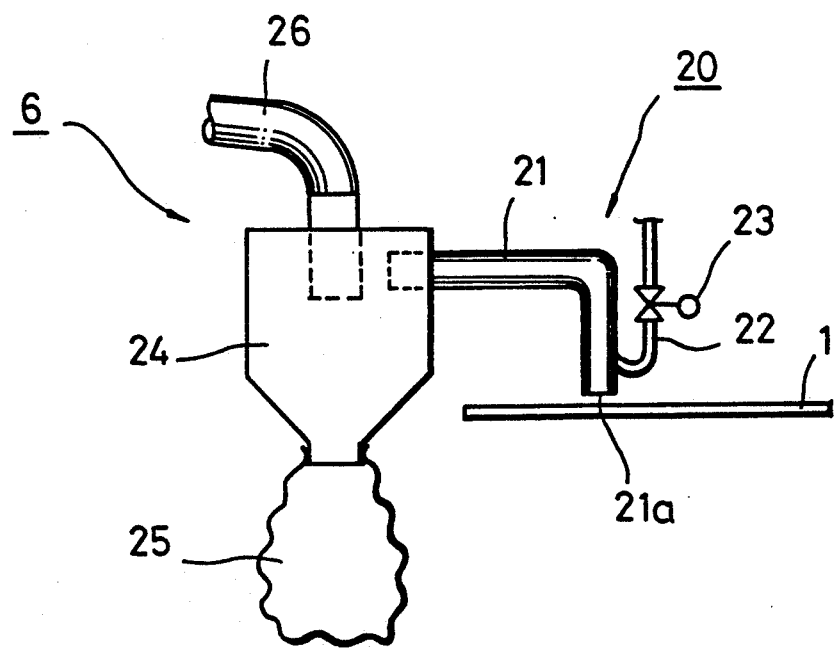
FIG. 12 is a view showing a portion of FIG. 7 indicated by an arrow XII.

As shown on FIG. 7, in the coloured foreign particle remover 5, suction ejector 17 is connected with cyclone 18 where the suction mouth of ejector 17 is placed close to and faces the top surface of rotary table 1 so that it absorbs the samples on the surface of rotary table 1 by the air (such as 4 kg/sqcm pneumatic pressure) that is sent from the air compressor (not shown in the drawing) to the ejector 17. Also, at the upper portion of cyclone 18, air blow off hose 19 is connected, whereas bag 18a (FIG. 2) that takes in the coloured foreign particles as separated from the air at cyclone 18, is connected to the bottom outlet of cyclone 18. Also, the coloured foreign particle remover 5 is installed in connection with the coloured foreign particle inspection system 4 and rotary drive mechanism 8 so that when the detected coloured foreign particles by the coloured foreign particle inspection system 4 come directly in front of the nozzle of ejector 17, it is absorbed by ejector 17. FIG. 12 shows the sample remover 6 seen to the arrow XII in FIG. 7. In FIG. 12, 20 designate generally a suction ejector which contains suction pipe 21, air supply pipe 22 and valve 23. One end of suction pipe 21 is connected to cyclone 24 and a suction opening 21a at its other end is close to the surface of rotary table 1 with the plane of the opening 21a being parallel to the rotary table surface 1 so that the sample on the rotary table surface is affirmatively absorbed. One end of the air supply pipe 22 is connected to the air compressor (not shown in the drawings) whereas the other end thereof is connected in a manner that it supplies the air in the opposite direction to the suction opening 21a while being placed at the opening 21a side of suction tube 21 and suction nozzle mouth 21a. Valve 23 adjusts the airflow in the air supply pipe 22. 25 is a polyethlene gab that is connected to the bottom side outlet of cyclone 24, 26 is the air blow off hose that is placed and connected to the upper part of cyclone 24, where this hose 26 is connected to the dust trap (not shown in the drawings) together with hose 19 of the coloured foreign particle remover 5. Further, sample remover 7 is of the same structure to sample remover 6. Also, on FIG. 2 the structure of the system that supplies the sample to hopper 12 is the same as the example as shown on FIG. 1. In other words, hopper 12 is placed so that it passes through frame 41 above top of hopper 12 and cyclone 43 is placed at the top opening of hopper 42 while loadcell 44 is secured on frame 41. To the side part of cyclone 43, one end of the sample transfer tube 45 is connected via the blow off nozzle 46. The other end of the sample transfer tube 45 is connected with sampling nozzle (not shown) that samples the powder granule material from on-line (not shown) with open/close valve 47 installed on the way of transfer tube 45. Also, air blowoff tube 48 is connected with the upper part of cyclone 43. From the bottom outlet of hopper 42, connection tube 60 extends straight downwards to connect with hopper 12. At the upper portion of connection tube 60, ball valve 49 and valve control 50 which adjusts the former are installed, and at midway of the connection tube 60 a metal detector 61 which inspects the existence or not of metal foreign particles within the sample while it drops through the inside of connection tube 60 is installed. Further, the connection tube portion 60a at the outlet of the metal detector 61 is of a bellows structure. 51 designates the cover of hopper 12.

Also, on FIG. 2, 31 is the printer that prints out the inspection data, 32 is the monitor that displays the image from the television camera 14, 33 is the computer which controls the function of the entire apparatus and memorizes the inspection data, 33a is the keyboard for it, 34 is the image signal processor, and 35 is the image analyzer, which all are used to judge the coloured foreign particle number and size in the sample by conducting the image analysis of the image signals from the television camera 14. 36 is the strobo main unit that controls the cycle etc. of strobos 15a, 15b and 37 is the power source filter that controls the power.

At the next step, the functions of the apparatus according to the invention will be explained. On FIG. 2 in a condition that the open/close valve 47 is open, as the powder granule material that flows through the on-line (not shown) is sampled by the sampling nozzle (not shown) and is transferred through the sample transfer tube 45 with the air flow, the powder granule sample is blown into cyclone 43 through the blow out nozzle 46 and is separated from the air as it circles inside cyclone 43. The separated sample accumulates inside hopper 42, and the air is released from the air blow out tube 48. The accumulated volume of the sample is weighed by the loadcell 44, and with a predetermined volume of accumulation, the open/close valve 47 closes and the valve control 50 adjusts the ball valve 49 so that a predetermined volume of the sample from hopper 42 is continuously released for inspection and falls through connection tube 60. At this time, the existence or not of metal foreign particles within the sample is inspected by the metal detector 61. The fallen sample accumulates inside hopper 12. At the same time, the air inside hopper 12 is exhausted from connection tube portion 60a of a bellows construction.

The accumulated sample inside hopper 12 is cutout in predetermined volume at trough 11 which is vibrated by the magneto coil 13 as shown on FIG. 9, and is gradually transferred inside trough 11 towards the rotary table 1. The transferred sample granule falls inside the protruding tube portion 11a as shown on FIG. 10 and falls to fit in the groove 73 where such direction is controlled by the protruding piece 11c upon passing the opening 11b, and appears as fit and lined up in dual rows inside the groove 73 without pileup on each other.

The sample granule that is fit inside groove 73 is conveyed on the rotary table 1 at a certain rotating speed by the rotation drive mechanism 8 (FIG. 8), and first passes under the static electricity remover 3 (FIG. 7) where the static electricity thereof is removed, and then passes under the television camera 14 of the coloured foreign particle inspection system 4 (Fig. 11). At such time, the sample is intermittently irradiated by strobos 15a, 15b to be photosensed so that the coloured foreign particle number and size are measured. At this time, the glass plate 71 that constructs the rotary table 1 (FIG. 5) is transparent with the acrylic layer 72 being semi transparent, although somewhat weaker, strobo 15b irradiates the sample in groove 73 from the back side. In other words, the sample shall be irradiated upon from both of the front and back sides of the rotary table 1, so that on the surface of rotary table 1 or that is to say that on the surface of the acrylic film 72, there will be no shadow of the sample granule by the strobo lights. In addition, the layer thickness of the acrylic layer 72 at the tapered portion 72a, is worked to be a thickness so that no shade will be detected on the furface of the acrylic layer 72 even when it is irradiated by strobo 15b (FIG. 11) at the back side of rotary table 1 and photosensed from above by television camera 14. Therefore, no sample shadow or shade of groove 73 is erroneously detected as a coloured foreign particle.

Then the coloured foreign particle in the sample is absorbed by the suction ejector 17 at the coloured foreign particle remover 5 (FIG. 7) to be blown into cyclone 18 which is separated from the air, while cycling inside the cyclone 18. The separated coloured foreign particles will be accumulated inside bag 18a (FIG. 2) which is connected to cyclone 18 while the air is exhausted from air flow off hose 19.

The sample with the coloured foreign particles removed is suction removed from the surface of rotary table 1 by the sample remover 6 (FIG. 12) first. In other words, for instance, if air with 4 kg/sqcm pressure is sent into the suction tube 21 from the air compressor (not shown) a suction force is generated at suction mouth 21a where the sample on the rotary table 1 surface is absorbed and passes through suction tube 21 and is sent to the cyclone 24. Such sent sample is separated with the air while circulating inside cyclone 24 and then the separated sample is accumulated in bag 25 that is connected to cyclone 24, while the air is released from the air blowout hose 26. At this time, the surface of rotary table 1, that is, the surface of the acrylic layer 72 is hard, the rotary table 1 does not warp by the suction of the suction ejector 20 so that the suction nozzle 21a does not get choked. Also, since the rotary table 1 surface is flat and since the surface of suction nozzle 21a of ejector 20 is installed to be in parallel with the surface of rotary table 1, the suction power by ejector 20 will evenly effect the rotary table 1 surface so that all of the sample that is under the suction nozzle 21a of suction ejector 20, which is to say that the suction power evenly effects all of the sample granule inside groove 73. Further, the same sample suction removal is conducted by the sample remover 7.

As explained above, according to the powder granule sample inspection apparatus of the present invention, as the sample granule that is inspected will fit inside the groove 73, so that even when the rotary table 1 is impacted with vibration, the moving around of sample granule by rolling on the rotary table 1 surface is prevented and the entire volume of the supplied sample granule can be inspected by which the inspection data reliability is raised. Moreover, with the sample granule lined up in two rows for the inspection, the inspection system will regularly be able to inspect and process by the proper volumed sample being constantly conveyed for the inspection to conduct a favourable insepction so that the inspection data reliability is further elevated.

Further, the rotary table 1 is semi transparent, with an arrangement for 2 strobos 15a, 15b irradiating the rotary table 1 surface from the front and back sides thereof respectively for the inspection by the coloured foreign particle inspection system 4, with further making the layer thickness of the taper portion 72a of the acrylic layer 72 to a thickness so that no shade on the acrylic layer 72 surface is detected by the television camera 14 from above while the groove 73 portion of the rotary table 1 is irradiated from both front and back sides by strobos 15a and 15b respectively, the formation of shadows of sample or shade of groove 73 on the surface of rotary table 1 by the strobo irradiation is prevented. Therefore, erroneous judgements of such shadows as coloured foreign particle can be prevented so that the coloured foreign particle inspection reliability is improved.

Also, the surface of rotary table 1 is hard and flat so that it will not warp by the suction of the sample remover 6. Therefore, the suction nozzle 21a of the suction ejector 20 can be set at a near position to the surface of rotary table 1 where sample suction will be positive, at the same time the suction power of the sample remover 6 can evenly function against the rotary table 1 surface to make a practically perfect sample removal. Further, since the sample is removed by the same structured sample removers 6, 7 consecutively, a further complete sample removal is conducted.

Further, since the coloured foreign particles contained in the sample are removed by the coloured foreign particle remover 5 and accumulated in bag 18a a further detailed inspection on the characteristics of the coloured foreign particles can separately be commenced. While, in the above explained embodiment, the glass plate 71 and the semi transparent plastic which is the acrylic layer 72 in this case are used to make the rotary table 1 of a dual structure, the rotary table 1 also may be a single layer structure. In that case, the single layer structure is bent and worked to form a groove at a thickness that the groove shadow will not appear similar to the groove in the above mentioned embodiment.

Figure 13:
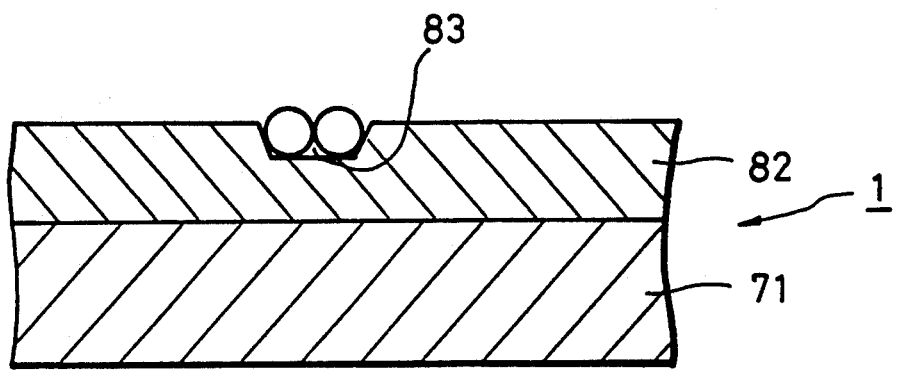
FIG. 13 is a partial cross-sectional view showing another example of the rotary table according to the present invention.
Figure 14:
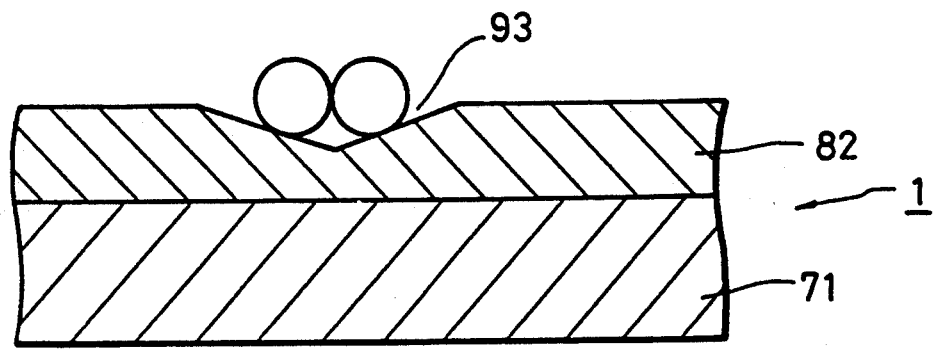
FIG. 14 is a partial cross-sectional view showing a further example of the rotary table according to the present invention.

Further, while the groove 73 is formed by bending and processing the acrylic layer 72, which in the case that coloured foreign particle inspection is not conducted, as shown as groove 83 on FIG. 13, it may be formed by cutting into the surface of acrylic plate 82 which is rather thicker than the above mentioned example. Also in such case, the shape of the groove need not necessarily be a reversed trapezoid cross section shape such as groove 73 or groove 83, it can be of any shape as long as the sample granule shall fit thereinto, for instance, it can be such as groove 93 on FIG. 14 with a cross section of a wide angle V shape. However, the groove depth must be smaller than the sample granule diameter. Needless to say, even in the case that the acrylic layer 72 is bent and worked to make the groove as in the aforementioned example, the groove shape is not limited to the reverse trapezoid cross section, and can be a V shape cross section. However, the thickness of layer at the groove portion 73 of acrylic layer 72 should be of a thickness that a shadow does not appear at the surface although irradiated by strobo from the back side.

Also the groove width is not limited so that two of the sample granules are fit to be lined up in rows, and it may be of a width for 1 each of a sample granule or if it is within the range where the inspection is done at one time by one inspection system, it could be such that more than 3 each be fit and lined up.

Further, although the rotary table 1 is formed by a dual structure of glass plate 71 and acrylic layer 72 in the aforementioned example, when coloured foreign particle inspection is not conducted, it can be structured by other material or it can be a single layer construction.

Also the shape of the rotary table does not have to be disc shaped.

Further, while the coloured foreign particle inspection system 4 only is installed to inspect the sample on the surface of rotary table 1, other equipment such as a moisture meter to measure the moisture content may be installed between the feeder system 2 and static electricity remover 3, or some further inspection system may be installed.

It will be apparent that many modifications and variations could be effected by one skilled in the art without departing from the spirits or the scope of the novel concepts of the present invention so that the spirits or scope of the invention should be determined by the appended claims only.

I claim as my invention:

1. Apparatus for continuously inspecting powder granule samples comprising a horizontally disposed rotatable flat table, said table being light transmissive and having an annular groove formed on its upper surface for receiving granules therein, means for rotating said table about a vertical axis, means for feeding a stream of granules into said groove and means for sensing the granules in said groove as said table is rotated, said means for feeding said granules and said means for sensing said granules being spaced from each other about the circumference of said groove, said means for sensing said granules comprising television camera and strobo light means which irradiate said rotary table from its top and bottom surfaces.

2. The apparatus according to claim 1, wherein said groove has inclined side walls.

3. The apparatus according to claim 2, wherein said groove has a cross section of an inverted trapezoid.

4. The apparatus according to claim 1, wherein said means for sensing the sample detects the number and size of colored foreign particles mixed in the sample.

5. The apparatus according to claim 1, wherein said rotary table is formed so that the wall thickness of said groove is so selected that no shadow is generated on the rotary table when it is irradiated by strobo light from the rear surface thereof.

* * * * *